United States Patent
Omori

(10) Patent No.: US 8,409,174 B2
(45) Date of Patent: Apr. 2, 2013

(54) MEDICAL MANIPULATOR SYSTEM

(75) Inventor: Shigeru Omori, Ashigarakami-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1264 days.

(21) Appl. No.: 12/178,082

(22) Filed: Jul. 23, 2008

(65) Prior Publication Data

US 2009/0036901 A1 Feb. 5, 2009

(30) Foreign Application Priority Data

Jul. 25, 2007 (JP) .................................. 2007-193528

(51) Int. Cl.
*A61B 17/00* (2006.01)
(52) U.S. Cl. .......................................... 606/1; 606/130
(58) Field of Classification Search ........................ 606/1
See application file for complete search history.

(56) References Cited

U.S. PATENT DOCUMENTS

| 5,792,165 | A | * | 8/1998 | Klieman et al. ............... 606/170 |
| 6,331,181 | B1 | | 12/2001 | Tierney et al. |
| 6,793,652 | B1 | * | 9/2004 | Whitman et al. ................. 606/1 |
| 7,314,473 | B2 | | 1/2008 | Jinno et al. |
| 7,784,663 | B2 | * | 8/2010 | Shelton, IV ................ 227/175.1 |
| 2004/0133189 | A1 | | 7/2004 | Sakurai |
| 2006/0212069 | A1 | * | 9/2006 | Shelton, IV .................... 606/205 |
| 2006/0278680 | A1 | * | 12/2006 | Viola et al. .................. 227/176.1 |
| 2008/0039255 | A1 | * | 2/2008 | Jinno et al. ..................... 474/148 |
| 2008/0300580 | A1 | * | 12/2008 | Shelton et al. ..................... 606/1 |

FOREIGN PATENT DOCUMENTS

| JP | 2004-105451 | 4/2004 |
| JP | 2004-208922 | 7/2004 |
| JP | 2005-103056 | 4/2005 |
| JP | 2006-254964 | 9/2006 |

* cited by examiner

*Primary Examiner* — Henry M Johnson, III
(74) *Attorney, Agent, or Firm* — Oblon, Spivak, McClelland, Maier & Neustadt, L.L.P.

(57) ABSTRACT

A medical manipulator system includes a medical manipulator, an operating unit for inputting operation commands, motors for driving a working unit, a controller for driving the motors based on operation commands supplied from the operating unit, and an LED that displays an operational state. The controller carries out controls for distinguishing between an operational mode in which the operation command is validated and the motors are driven, and a stopped mode in which the motors are halted regardless of whether the operation command is present or not. An illumination state of the LED is switched dependent on whether the system is in the operational mode or the stopped mode. The LED is disposed in the center of an upper surface of a bridge, which interconnects a grip handle and an actuator block.

4 Claims, 10 Drawing Sheets

MEDICAL MANIPULATOR SYSTEM

BACKGROUND OF THE INVENTION

1. Field of the Invention

The present invention relates to a medical manipulator system by which a predetermined working unit performs movements and operations based on operation commands input from an operating unit.

2. Description of the Related Art

In laparoscopic surgery, a number of small holes are opened in a patient's abdomen or the like, and an endoscope, a forceps (or manipulator) or the like is inserted, and surgery is carried out while the surgeon observes an image from the endoscope on a monitor. In this type of laparoscopic surgery, owing to the fact that opening of the abdominal cavity is unnecessary, the burden on the patient is small, and number of days for the post-operative recovery and number of days spent in the hospital can be significantly reduced. Therefore, laparoscopic surgical operations are expected to find an increased range of applications.

A manipulator system, for example, as disclosed in Japanese Laid-Open Patent Publication No. 2004-105451, comprises a manipulator main body, and a controller for controlling the main body. The manipulator main body comprises an operating unit, which is operable by hand, and a working unit, which is detachable and exchangeable with respect to the operating unit.

The working unit (tool) includes an elongate connecting shaft, and a distal end working unit (also referred to as an "end effector") disposed at the end of the connecting shaft. One or more actuators (motors) are disposed in an operating unit for driving the distal end working unit by means of wires. The wires are trained around pulleys at a base end side. The controller drives the motors disposed in the operating unit, and also drives the wires in an advancing/retracting manner via the pulleys.

Because of the necessity to easily clean and disinfect the working unit periodically, the working unit does not contain any electronic components such as sensors or the like, and the positions and origin points of the distal end working unit and the base end pulleys cannot be detected directly. Rather, a structure is provided in which the axial positions (posture) of the distal end working unit are calculated based on a rotation amount of the motors.

Incidentally, in laparoscopic surgery, various different types of working units are used depending on the surgery involved. A gripper, a cutter, an electrical knife, an ultrasonic knife, a surgical drill, or the like may be given as examples thereof. Such working units are disposed detachably with respect to the operating unit, and a structure is provided, such that when installed, the pulleys on the base end side of the working unit engage with rotary axes of the motors disposed in the operating unit.

In this manner, in the case of a system, which is predicated on enabling the connection of multiple different types of working units with respect to a single operating unit, it is necessary to set the motor phases such that all of the working units can be attached and detached while maintaining a sole common axial-positioning thereof (see, e.g., Japanese Laid-Open Patent Publication No. 2004-105451). Such axial positioning is referred to as an origin point (or an initial position).

Further, when it is desired to exchange the distal end working unit with another type, it is advisable also to exchange the manipulator main body. In this case, a connector, which connects the controller and the operating unit of the manipulator main body, is disconnected, and another connector of a different manipulator main body is reconnected.

With general manipulators available in the industry, although the manipulator and the controller are not disconnected (cut off) while the system is in use (i.e., during system operation), for medical use, it is preferable for detachment (cutting off) between the manipulator and the control apparatus to be easily carried out, since as indicated above, multiple different types of working units are utilized with the manipulator.

The following may be cited as conventional techniques concerning manipulator control systems: Japanese Laid-Open Patent Publication No. 2004-105451, Japanese Laid-Open Patent Publication No. 2004-208922, and U.S. Pat. No. 6,331,181.

Japanese Laid-Open Patent Publication No. 2004-105451 proposes a structure in which it is unnecessary to consider switching of the motor excitation or electrical configurations at the time of detachment.

Japanese Laid-Open Patent Publication No. 2004-208922 discloses features related to electrical detachment of plural end tools (working units).

According to U.S. Pat. No. 6,331,181, in relation to attachment and detachment of a medical manipulator, a circuit is included in a front-end manipulator for extracting an ID, wherein controls are carried out by the control apparatus based on obtaining such information.

Incidentally, as described above, the axial positioning of the distal end working unit is calculated taking as a standard the origin point thereof, for example. Accordingly, in the case that the working unit is exchanged during an operation, it is essential for the axial positioning of the newly installed and different working unit to match with the origin point accurately. Stated otherwise, when the working unit is separated from the operating unit, it is desirable that the working unit be placed in an axial position that matches with the origin point thereof. In particular, when the manipulator is in an operational mode, caution must be taken so that the connector that connects the operating unit and controller of the manipulator cannot be pulled out.

Further, in the event that the distal end working unit of the manipulator is to be taken out of the body, it is necessary to halt the operations thereof beforehand. For this purpose, based on a switching operation or the like in the controller, both an operational mode in which the motors are driven, and a stopped mode in which the motors are halted irrespective of whether operations of the operating unit are present or not, are provided, wherein preferably the control is carried out by distinguishing between these modes. Based on such switching operations or the like, preferably, the operator can easily confirm switching between the operational mode and the stopped mode.

SUMMARY OF THE INVENTION

The present invention has the object of providing a medical manipulator system, which enables the changing of operational modes and detachment of a connector or the like to be suitably controlled.

A medical manipulator system according to one aspect of the present invention comprises a medical manipulator, a controller, and at least one indicator for indicating an operational state of the medical manipulator, the medical manipulator including an operating unit, which is equipped with at least one of the indicators, an actuator, a grip handle that is gripped manually, and an input unit for inputting operation commands, and further including a working unit being detachable with respect to the actuator and being equipped with a distal end working unit, the distal end working unit being operatively coupled to the actuator at an end of a shaft, and being rotated about a pivot axis that is non-parallel with an axis of the shaft, wherein the controller controls the actuator based on an operation command supplied from the input unit, and a control is carried out for distinguishing at least between an operational mode in which the operation command is validated and the actuator is driven, and a stopped mode in which the actuator is halted regardless of whether the operation command is present or not, an illuminated state of the indicator being switched by the operational mode and the stopped mode.

By providing such an indicator, the operator can easily confirm at least the operational mode and the stopped mode, and therefore surgical operations can be carried out efficiently. Switching of the illumination state may be defined as switching between an illuminated and a non-illuminated state, switching between continuous illumination and a flashing state, switching a flashing cycle, switching the illumination brightness, or the like.

Further, a medical manipulator system according to another aspect of the present invention comprises a medical manipulator and a controller, the medical manipulator including an operating unit, which is equipped with an actuator, a grip handle that is gripped manually, and an input unit for inputting operation commands, and further including a working unit being detachable with respect to the actuator and being equipped with a distal end working unit, the distal end working unit being operatively coupled to the actuator at an end of a shaft, and being rotated about a pivot axis that is non-parallel with an axis of the shaft, wherein the controller comprises a connector interconnecting the operating unit and the controller, and a lock mechanism for preventing pulling out and disconnection of the connected connector, and further wherein the controller controls the actuator based on an operation command supplied from the input unit, whereby a control is carried out for distinguishing at least between an operational mode in which the operation command is validated and the actuator is driven, and a stopped mode in which the actuator is halted regardless of whether the operation command is present or not, the controller locking the lock mechanism during the operational mode.

In this manner, in the case of the operational mode, by means of the lock mechanism locking the connector that interconnects the operating unit and the controller, the connector cannot be inadvertently pulled out and disconnected.

The above and other objects features and advantages of the present invention will become more apparent from the following description when taken in conjunction with the accompanying drawings, in which a preferred embodiment of the present invention is shown by way of illustrative example.

DESCRIPTION OF THE PREFERRED EMBODIMENTS

Descriptions of a medical manipulator system 500 according to an embodiment of the present invention shall be presented below with reference to the accompanying FIGS. 1 through 10. The manipulator system 500 (see FIG. 1) is intended for medical use, and in particular is utilized for performing laparoscopic surgeries and the like.

Figure 1:
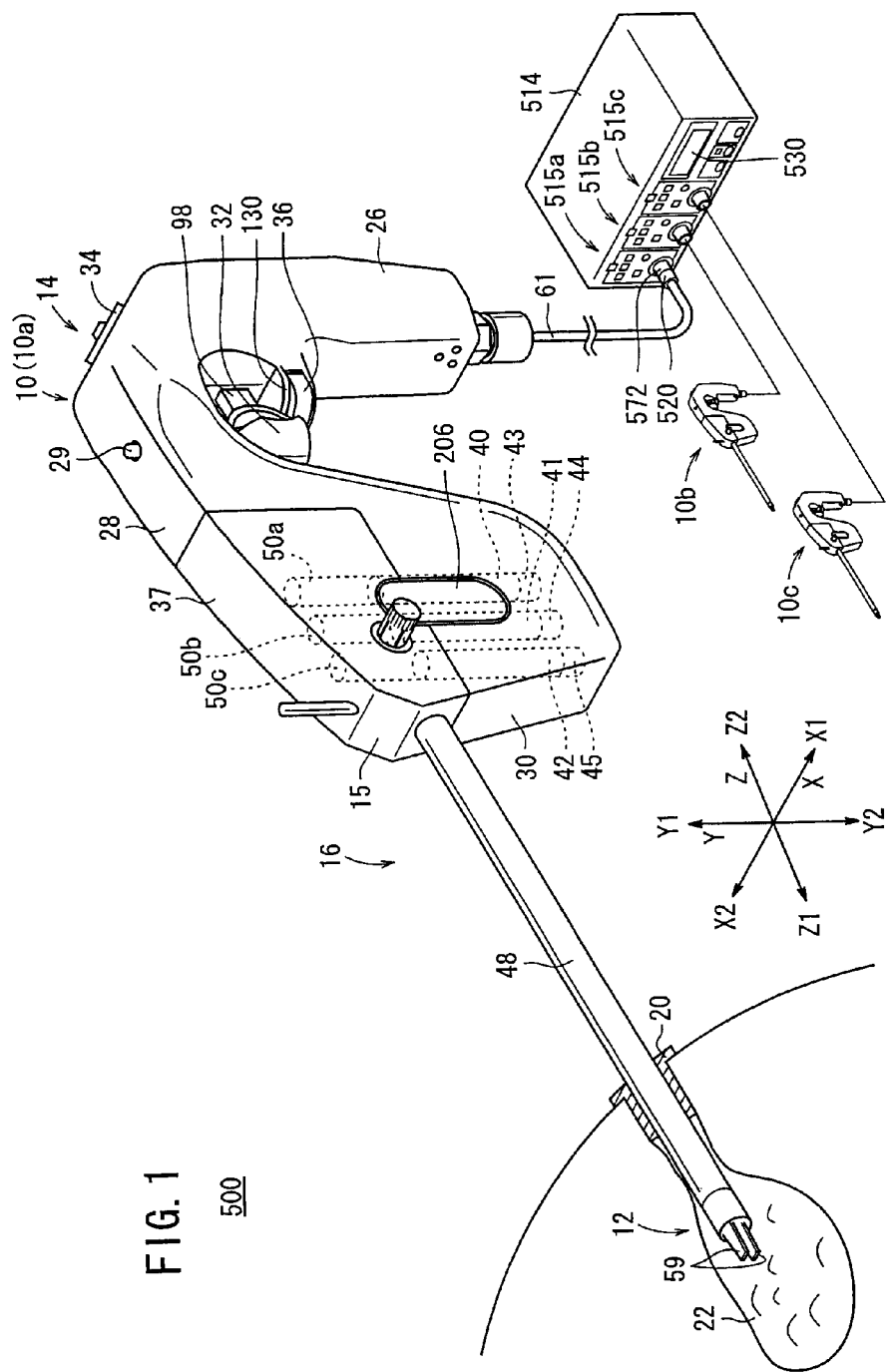
FIG. 1 is an outline structural view of a manipulator system according to an embodiment of the present invention.

As shown in FIG. 1, the manipulator system 500 includes a manipulator 10 and a controller 514.

To interconnect the manipulator 10 and the controller 514, a detachable connector 520 is provided.

A distal end working unit (end effector) 12 of the manipulator 10 carries out predetermined procedures for gripping a portion of a living body or a curved needle, or the like. The basic structure of the manipulator 10 is made up from an operating unit 14 and a working unit 16. The controller 514 serves to carry out electrical controls for the manipulator 10, and is connected through a connector 520 with respect to a cable 61 that extends from a lower region of a grip handle 26.

The controller 514 can control three manipulators 10 independently and simultaneously. On the controller 514, first, second and third portions thereof for controlling the manipulator 10 may also be referred to overall as a first port 515a, a second port 515b and a third port 515c. The manipulators 10, which are connected to the first port 515a, the second port 515b and the third port 515c, are referred to and distinguished respectively when necessary as a manipulator 10a, a manipulator 10b and a manipulator 10c (see FIG. 1).

Figure 2:
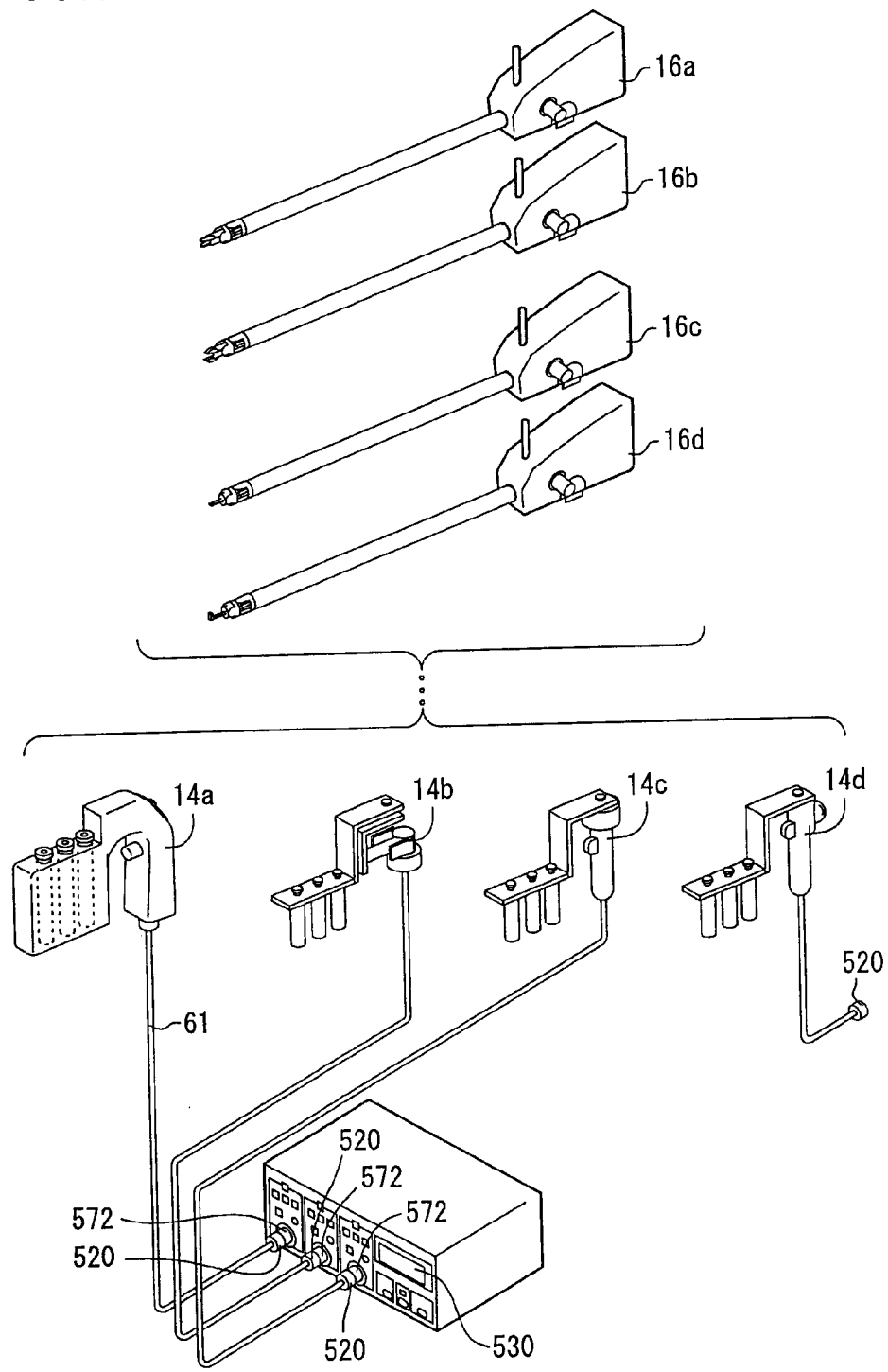
FIG. 2 is an explanatory diagram pertaining to assembly of a structure of the manipulator system according to the embodiment of the present invention.

As shown in FIG. 2, the manipulator system 500 may adopt various configurations selectively. Specifically, in the controller 514, for the operating unit 14, different operating units 14a to 14d may be prepared as variations thereof. Further, for the working unit 16, different working units 16a to 16d may be prepared as variations thereof.

On the controller 514, in place of the operating unit 14a, the operating units 14b, 14c and 14d can be installed. Further, with respect to each of the operating units 14a to 14d, in place of the working unit 16a, the working units 16b, 16c and 16d can be installed. More specifically, depending on the conditions such as types of and proficiency in the surgical technique, the surgeon can selectively combine and configure the operating units 14a to 14d and the working units 16a to 16d. Thereamong, on the working unit 16b, the distal end working unit 12 functions as a cutter, on the working unit 16c, the distal end working unit 12 thereof functions as a blade type electrosurgical knife, and on the working unit 16d, the distal end working unit 12 functions as a hook type electrosurgical knife. In each of the working units 16a-16d, pulleys 50a, 50b and 50c inside a connector 15 (see FIG. 1) have a common structure and configuration.

In accordance with the structures described above, since the controller 514 is capable of simultaneously controlling three manipulators 10, among the operating units 14a to 14d, any three thereof can be connected to the first port 515a, the second port 515b, and the third port 515c.

Next, the manipulator 10 made up from the operating unit 14 and the working unit 16 shall be described.

The manipulator 10 is used for performing prescribed treatments by gripping a part of a living body or a curved needle or the like by the distal end working unit 12, which typically is referred to as a grasping forceps or a needle driver (needle holder).

Figure 3:
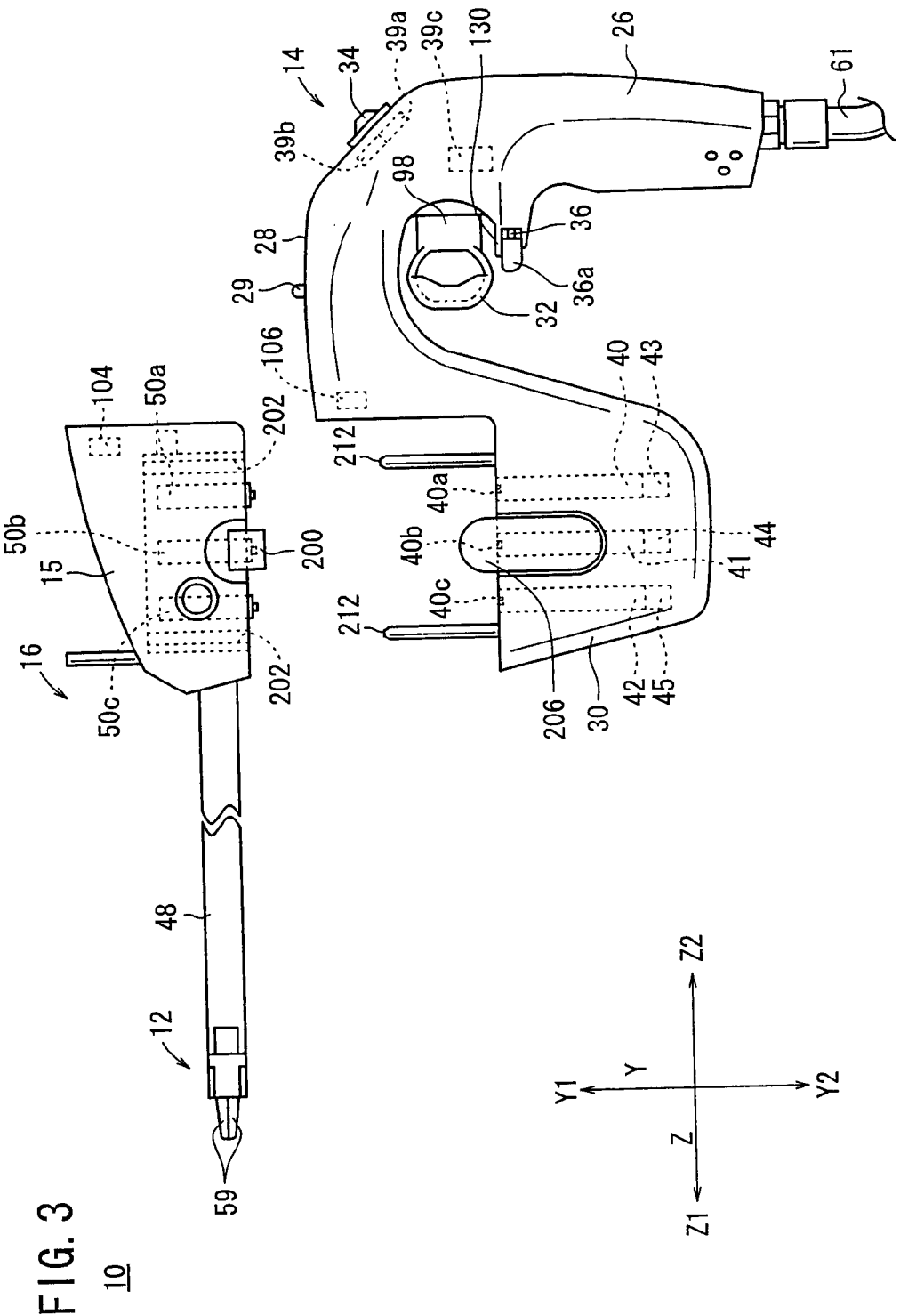
FIG. 3 is a side surface view of the manipulator in which the working unit and the operating unit are separated from each other.

As shown in FIGS. 1 and 3, the manipulator 10 includes the operating unit 14, which is held and operated by hand, and the working unit 16, which is detachable with respect to the operating unit 14.

It shall be assumed in the following descriptions that, as shown in FIG. 1, the transverse direction is defined as an X direction, the vertical direction thereof as a Y direction, and the longitudinal directions of the connecting shaft 48 as a Z direction. Further, among the X directions, the rightward direction is defined as an X1 direction, and the leftward direction as an X2 direction. Among the Y directions, the upward direction is defined as a Y1 direction, and the downward direction as a Z1 direction. Among the Z directions, the forward direction is defined as a Z1 direction, and the rearward direction as a Z2 direction. Moreover, unless otherwise noted, these directions represent directions of the manipulator 10 when it is in a neutral posture. The definitions of the above directions are for illustrative purposes only, and the manipulator 10 can be used in any of various orientations (e.g., the manipulator may be used upside down).

The working unit 16 includes the work-performing distal end working unit 12, a connector 15 connected to the actuator block (actuator unit) 30 of the operating unit 14, and a hollow connecting shaft 48 of a given length dimension connected between the distal end working unit 12 and the connector 15. The working unit 16 is capable of being detached from the operating unit 14 by means of a predetermined operation in the actuator block 30, wherein cleaning, disinfection, maintenance and the like can be carried out thereon.

The distal end working unit 12 and the connecting shaft 48 are narrow in diameter, and can be inserted into a body cavity 22 through a trocar 20 in the form of a hollow cylinder mounted inside an abdominal region or the like of the patient. By operations of the operating unit 14, various techniques can be performed to grip, remove, suture, or ligate an affected part of the patient's body within the body cavity 22.

The operating unit 14 includes a grip handle 26, which is gripped by hand, a bridge 28 extending from an upper portion of the grip handle 26, and the actuator block 30, which is connected to a distal end of the bridge 28.

As shown in FIG. 1, the grip handle 26 of the operating unit 14 extends in the Z1 direction from the end of the bridge 28, and has a length suitable for being gripped by hand, and further includes a trigger lever 32 functioning as an input means, a compound input unit 34, and a switch 36.

An LED (indicator) 29 is disposed at a location capable of being easily confirmed on an upper surface (or a side surface) of the bridge 28. The LED 29 is an indicator for displaying the control state of the manipulator 10, having a size to enable easy recognition thereof by the operator, and further being sufficiently small in size and light in weight so as not to obstruct operations performed by the manipulator 10. The LED 29 is disposed roughly in a central position on the upper surface of the bridge 28, at a position where visual confirmation thereof is easy.

A cable 61 connected to the controller 514 is disposed on a lower end of the grip handle 26. The grip handle 26 and the cable 61 may be connected to each other integrally or through a connector.

The compound input unit 34 makes up a compound input means for imparting rotational commands in rolling (shaft rotating) and yawing (left and right) directions to the distal end working unit 12. For example, commands in the rolling direction are given by a first input means, which operate in the shaft rotating direction, whereas commands in the yawing direction are given by a second input means, which operate in the lateral direction. The trigger lever 32 comprises an input means for imparting opening and closing commands for the gripper 59 (see FIG. 1) of the distal end working unit 12. The switch 36 serves as an input means for setting valid and invalid states in relation to the operating conditions of the manipulator 10.

Figure 4:
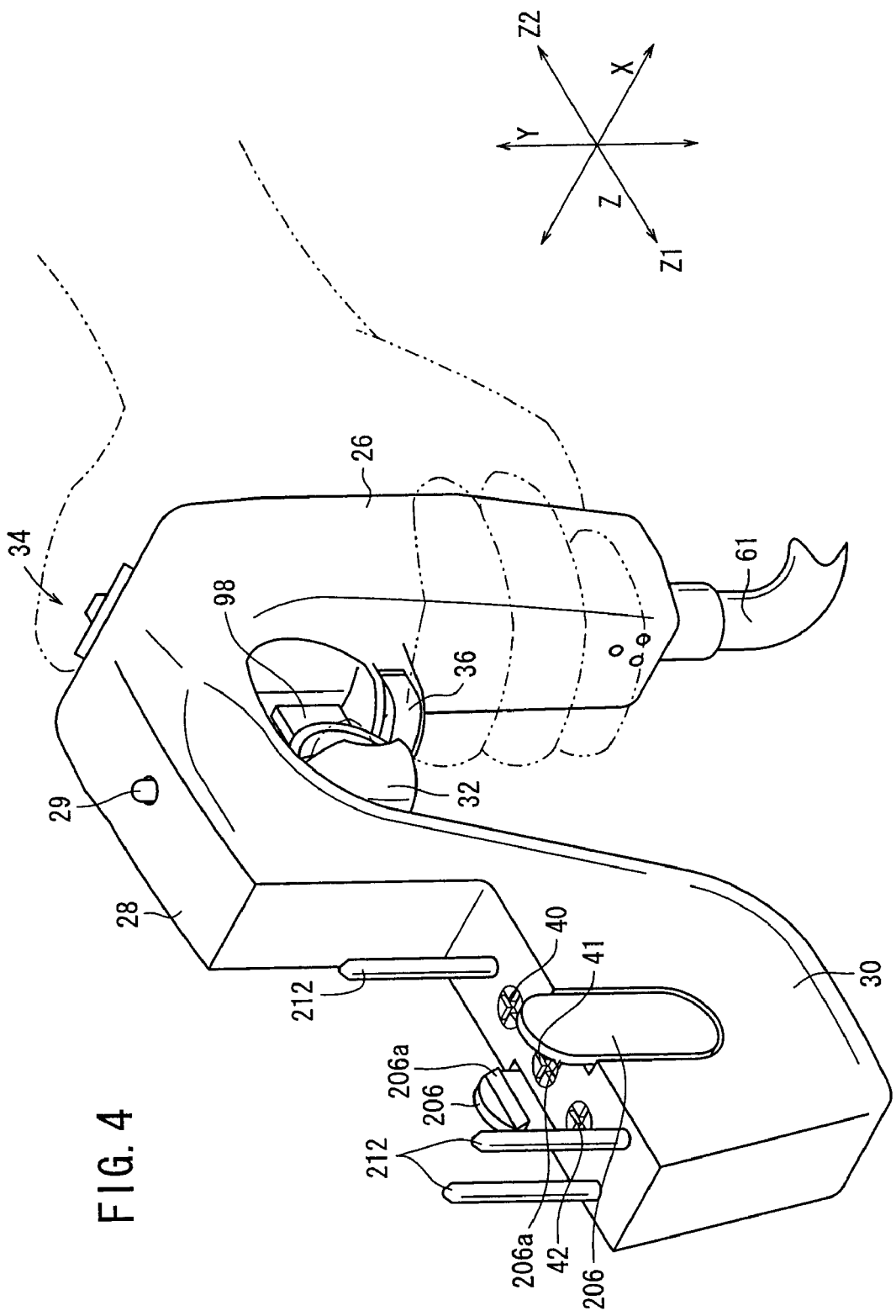
FIG. 4 is a perspective view of the operating unit.

As shown in FIGS. 3 and 4, the compound input unit 34 and the trigger lever 32 include input sensors 39a, 39b, 39c for detecting respective operating values, and supplies detection operation signals (e.g., an analog signal) to the controller 514.

The trigger lever 32 comprises a lever that juts out slightly in the Z1 direction from below the bridge 28, and is disposed at a position where it can easily be operated by the index finger.

The trigger lever 32 is connected by an arm 98 with respect to the grip handle 26, and is movable toward and away from the grip handle 26.

The switch 36 is an operating mechanism, which is movable toward and away from the grip handle 26. The trigger lever 32 and the switch 36 are disposed alongside one another in a lengthwise direction (Y direction) of the grip handle 26, on a surface facing in the Z1 direction on the grip handle 26. The switch 36 is disposed directly underneath the trigger lever 32 (in the Y2 direction). A thin-plate member 130 is disposed between the switch 36 and the trigger lever 32.

The switch 36 alternately is placed in a locked ON condition (first condition) by pulling the switch 36 inwardly (in the Z2 direction), wherein once pulled, the operating element 36a thereof is retained toward the side where the switch 36 is pulled in. By pulling the switch 36 inwardly again a second time, the ON condition is released, whereby the switch 36 is placed in an OFF condition (second condition), the switch 36 being restored to the position facing the distal end side (in the Z1 direction) by an unillustrated resilient body. As a result of these operations, the switch 36 is retained in either one of the ON condition or the OFF condition, and it is unnecessary for the switch 36 to be pressed continuously. Accordingly, the switch 36 can be operated easily only at a time when the ON condition and the OFF condition are switched, and at other times, the trigger lever 32 can be operated, whereby the cooperative working relationship between the switch 36 and the trigger lever 32 is favorable.

Further, because the outward jutting amount of the operating element 36a differs between the ON condition and the OFF condition of the switch 36, simply by observing and/or touching the operating element 36a, the condition of the switch 36 can easily be confirmed.

The switch 36 operates as a means for changing between modes. The mode condition is displayed by the illuminated state of the LED 29, as well as by illumination of the port number lamps 560 (see FIG. 7) which shall be discussed later. Specifically, the LED 29 and the port number lamps 560 are illuminated in green during the operational mode, and are extinguished during the stopped mode. Further, during an automated origin point restoring operation, or during a resetting operation, the LED 29 and the port number lamps 560 flash in green, whereas during generation of an alarm state, the LED 29 and the port number lamps 560 flash in red.

The aforementioned modes and operations are changed through operating the switch 36. That is, the controller 514 reads in the state of the switch 36, and when in the ON state, initiates the operational mode, and when switched from the ON state to the OFF state, the motors (actuators) 40, 41, 42 are returned to their predetermined origin points in an automated origin point restoring operation, and after returning to their origin points, the controller 514 places the system in the stopped mode.

The operational mode is defined as a mode in which the operation commands of the operating unit 14 are validated and the motors 40, 41, 42 are driven. The stopped mode is defined as a mode in which the motors 40, 41, 42 are halted, regardless of whether an operation command from the operating unit 14 is present or not. Further, the reset operation is defined as an operation in which, when a predetermined operation takes place (to be described later), the motors 40, 41, 42 are automatically returned to their predetermined origin points. The automated origin point restoring operation and the reset operation act to operate the motors 40, 41, 42 regardless of whether an operation command from the operating unit 14 is present or not, and therefore both are classified as automatic modes.

The aforementioned modes and operations are distinguished and controlled by the controller 514, whereupon the illumination states of the LED 29 and the port number lamps 560 are switched.

The actuator block 30 houses the motors 40, 41, 42 therein corresponding to the respective mechanisms having three degrees of freedom, which are incorporated in the distal end working unit 12. The motors 40, 41, 42 are arrayed in parallel with each other in the longitudinal direction of the connecting shaft 48. The motors 40, 41, 42 are small in size and narrow in diameter, thus enabling the actuator block 30 to be compact and flat in shape. The actuator block 30 is disposed underneath the end of the operating unit 14 in the Z1 direction. Further, the motors 40, 41, 42 are energized to rotate drive shafts thereof under the control of the controller 514, based on operations of the operating unit 14.

The motors 40, 41, 42 are combined with angle sensors 43, 44, 45, capable of detecting rotational angles and supplying the detected angle signals to the controller 514. The angle sensors 43, 44, 45 may comprise and utilize rotary encoders, for example.

The working unit 16 includes the connector 15 joined with respect to the actuator block 30, and the hollow connecting shaft 48 extending in the Z1 direction from the connector 15. The connector 15 houses pulleys 50a, 50b, 50c rotatably therein, which are connected respectively to the drive shafts of the motors 40, 41, 42. Couplings are disposed respectively on each of the pulleys 50a, 50b, 50c.

Wires 52, 53, 54 are trained respectively around the pulleys 50a, 50b, 50c and extend through a hollow space 48a (see FIG. 5) in the connecting shaft 48 to the distal end working unit 12. The wires 52, 53, 54 may be of the same type and have the same diameter.

The working unit 16 is capable of being detached from the operating unit 14 through a predetermined operation in the actuator block 30, for enabling cleaning, sterilization, maintenance and the like to be performed thereon. Further, the working unit 16 can be replaced by another working unit of a different type, and further, depending on the surgical technique being performed, another connecting shaft 48 having a different length, or another distal end working unit 12 having a different mechanism, can be installed thereon.

The working unit 16 is detachable with respect to the operating unit 14, with a structure in which the rotating drive shafts 40a, 41a, 42a of the motors 40, 41, 42 are fitted into central holes disposed in the pulleys 50a, 50b, 50c. Respective cross-shaped projections are provided on a lower end in the Z1 direction of the pulleys 50a, 50b, 50c, and respective cross-shaped engaging recesses are provided on the rotating drive shafts 40a, 41a, 42a of the motors 40, 41, 42. The engaging projections and engagement recesses are capable of engagement with one another, so that rotations of the motors 40, 41, 42 are transmitted securely to the pulleys 50a, 50b, 50c. An ID retaining section 104, which holds an ID capable of individually distinguishing between the working units, is disposed on the connector 15.

The ID retaining section 104 may be configured as a wireless system, for example, an RFID (Radio Frequency Identification) type or the like, a non-contact detection system such as an optical type for detecting a barcode or a matrix type two-dimensional code or the like, or a contact type that detects an array of projections or the like.

In the event that a writable storage medium, such as an RFID or the like, is utilized in the working unit 16, individualized information may be stored on a case-by-case basis, such as the manufacturing date, the date of first use, date of last use, timestamps or serial numbers pertaining to maintenance dates, etc., an upper limit on the number of times of use, phase correction values (or origin point correction values) or the like. Such information may be read in by the controller 514 and displayed on an operating state display device 530 (see FIG. 1), or may be utilized to generate various cautions or warnings by carrying out predetermined judgment procedures.

In the ID stored in the ID retaining section 104, each of the working units is given a different ID value that enables it to be distinguished from the others.

Incidentally, in the case that the ID retaining section 104 is constituted by an RFID or a two dimensional matrix type code, etc., it is not necessary for the ID retaining section 104 to be electrically energized, and no electrical contacts exist within the connector 15 and the working units 16. Accordingly, cleaning and sterilization or the like can easily be carried out on the working units 16 when detached from the operating unit 14. More specifically, electrical components such as motors, switches, sensors and the like are all arranged on the side of the operating unit 14, and by disposing the connecting shaft 48 and distal end working unit 12, which are made up only of mechanical elements, all on the side of the working unit 16, cleanliness as well as the ability to clean the device are improved. The manner and types of ways under which the working unit 16 and the operating unit 14 become dirty or contaminated, as well as the cleaning methods therefor, differ from one another, and thus in order to carry out different maintenance operations thereon, it is preferable for them to be detachable from each other.

The operating unit 14 includes an ID relay 106, which reads the information in the ID retaining section 104 of the working unit 16 connected thereto and supplies such information to the controller 514. The ID relay 106 may be constituted by an RFID transmitting/receiving circuit, a photocoupler, or the like.

When a magnetic, optical or electrical wave method is utilized, the ID retaining section 104 can transmit the ID in a non-contact manner with respect to the ID relay 106, whereby the durability of the ID retaining section 104 and the ID relay 106 is heightened, contamination is reduced, and cleaning and washing thereof is made easier.

In the case that the connector 15 is detached from the operating unit 14, levers 206 disposed on both side surfaces of the actuator block 30 are pressed and tilted so as to be opened respectively outward, whereupon wedge members 206*a* on the levers 206 are released from engaging tabs 200 disposed on both sides of the connector 15, and accordingly, the connector 15 can be pulled upwardly (in the Y1 direction) off from the operating unit 14 and be separated therefrom. Three alignment pins 212 are provided on the upper surface of the actuator block 30, whereby the connector 15 is capable of being stably retained by engagement of the alignment pins 212 into engagement holes 202 disposed on the connector 15. When the connector 15 is installed onto the operating unit 14, the three alignment pins 212 are aligned with and fitted respectively into the engagement holes 202, and the connector 15 is pressed downward (in the Y2 direction). As a result, the levers 206 expand outwardly at first, and then after returning to their original positions, the connection is completed upon engagement of the levers 206 with the engaging tabs 200.

Figure 5:
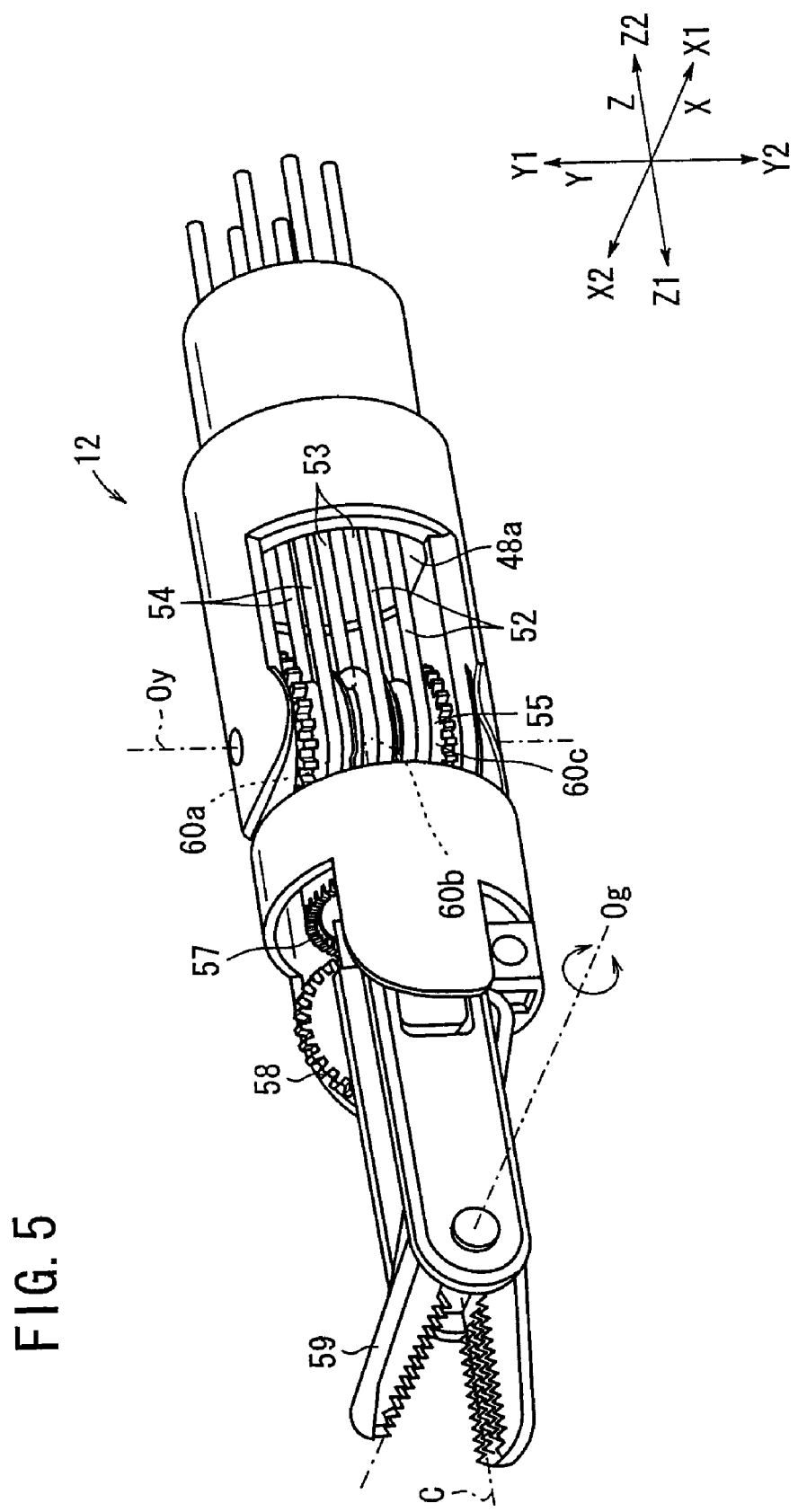
FIG. 5 is a perspective view of the working unit and the end effector of the manipulator.
Figure 6:
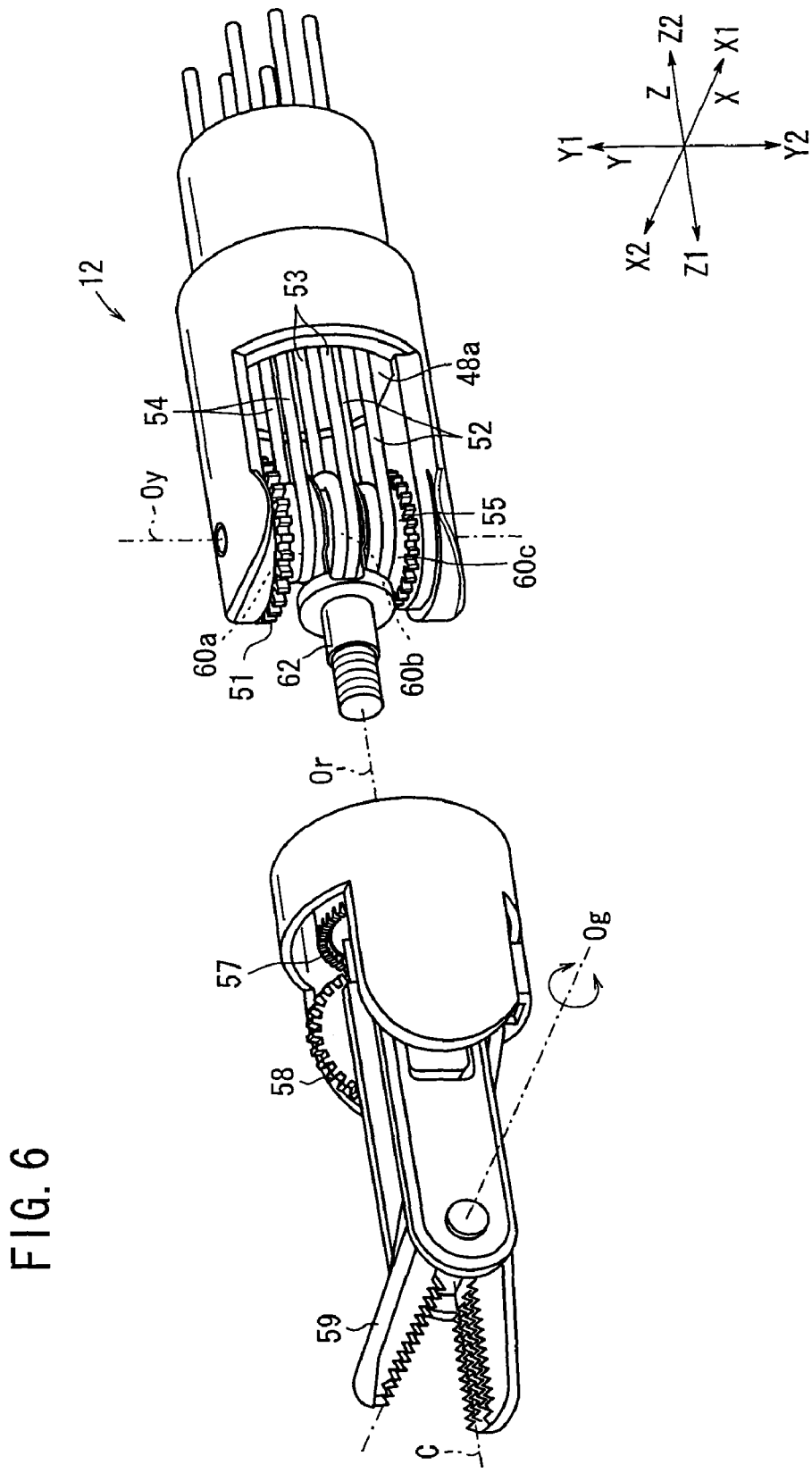
FIG. 6 is a perspective view of the manipulator, wherein the working unit and the end effector are separated from each other.

As shown in FIGS. 5 and 6, the distal end working unit 12 incorporates therein mechanisms providing three degrees of freedom. These mechanisms include a mechanism (tilting mechanism, pivot shaft) having a first degree of freedom for angularly moving a distal end portion that is positioned ahead of a first rotational axis Oy extending along the Y-axis direction in yawing directions about the first rotational axis Oy, a mechanism (rolling mechanism) having a second degree of freedom for angularly moving the distal end portion in rolling directions about a second rotational axis Or, and a mechanism for opening and closing the gripper 59 about a third rotational axis Og.

The first rotational axis Oy of the mechanism having the first degree of freedom may extend non-parallel to an axis C, which extends from the proximal end side to the distal end side of the connecting shaft 48. The second rotational axis Or of the mechanism having the second degree of freedom may be made up of a mechanism capable of rotating about an axis that extends along the axis of the distal end working unit 12 at the tip end, i.e., at the gripper 59 thereof, so that the gripper 59 can roll around the second rotational axis Or.

The distal end working unit 12 is actuated by the wires 52, 53, 54 that are trained around respective cylindrical bodies 60*c*, 60*b*, 60*a* disposed in the distal end working unit 12.

In the distal end working unit 12, under actions of the wires 52 and 54, gears 51 and 55 in the distal end working unit 12 are rotated to rotate an unillustrated face gear in mesh therewith, thereby turning the distal end portion in rolling directions. Further, under an action of the wire 54, a gear 51 in the distal end working unit 12 is rotated, whereby the gripper 59 can be opened and closed through a face gear 57 and another gear 58 enmeshed therewith. Moreover, under actions of the wires 52, 53, 54, the distal end portion can be made to turn in yawing directions through a main shaft 62.

Next, the controller 514 of the present invention shall be described below with reference to FIGS. 7 and 8.

Figure 7:
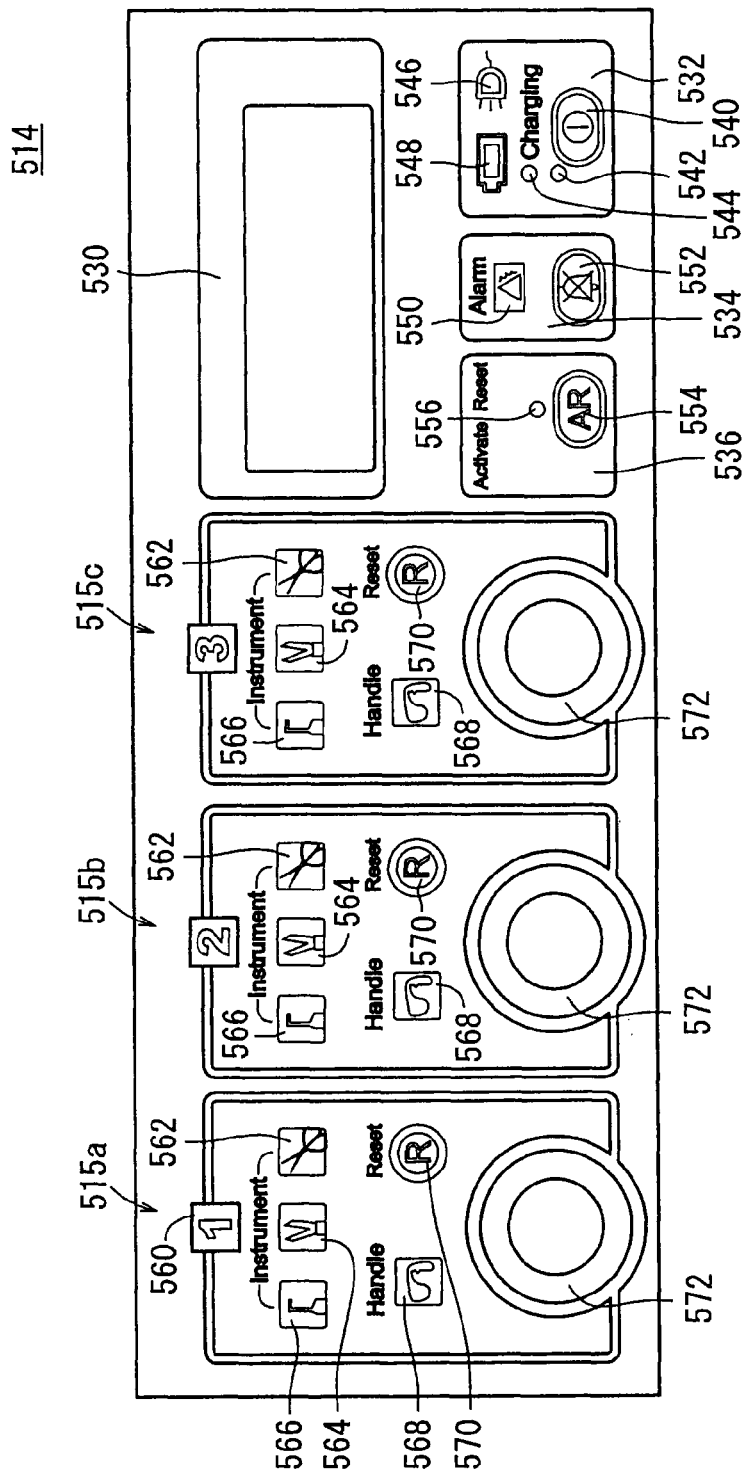
FIG. 7 is a front surface view of a controller.

As shown in FIG. 7, on the front surface of the controller 514, there are provided an operating state display device 530, a power source information display unit 532, an alarm unit 534, an activate reset unit 536, a first port 515*a*, a second port 515*b*, and a third port 515*c*.

The operating state display device 530 includes a liquid crystal display for displaying the operating state of the manipulator 10, or other predetermined responsive indications, thereby enabling easy recognition by the surgeon or a surgical assistant of the manipulated state thereof.

The power source information display unit 532 includes a power source switch 540, a power source lamp 542, a charging lamp 544, an external power source warning lamp 546, and a battery charging display lamp 548.

The power source switch 540 is a switch for turning on and cutting off supply of electrical power to the overall manipulator system 500. The power source lamp 542 is illuminated when the power supply is turned ON, and is extinguished when the power supply is turned OFF. The charging lamp 544 is illuminated at a time when charging is carried out with respect to a battery 112*a* (see FIG. 8). The external power source warning lamp 546 becomes illuminated at a time when power from the external power source 119 cannot be supplied. The battery charging display lamp 548 displays a remaining amount of power by changing a number of illuminated elements, or an illumination color, etc., in accordance with a charge amount of the battery 112*a*.

The alarm unit 534 includes an alarm lamp 550 and an alarm sound stopping switch 552. The alarm lamp 550 is illuminated upon generation of an alarm state, which is illuminated simultaneously with a buzzer sound of a separately installed alarm buzzer. The alarm sound stopping switch 552 is a push-button switch for stopping the buzzer sound of the alarm buzzer as may be needed.

The activate reset unit 536 includes an activate reset switch 554 and a reset indicator lamp 556. The reset indicator lamp 556 is illuminated at a given timing at which execution of a reset operation is carried out, for forcibly restoring each of the motors 40, 41, 42 of the manipulator 10 to their predetermined origin points. The activate reset switch 554, by being pressed when the reset indicator lamp is illuminated, is a switch for indicating a first reset operation.

The first port 515*a* includes a port number lamp 560, three working unit type distinguishing lamps 562, 564, 566, and a connection confirmation lamp 568 for the operating unit 14, a reset switch 570, and a receptacle connector 572. The connector 520 is connected to the receptacle connector 572.

The number "1" is printed on the port number lamp 560, which is illuminated when a corresponding manipulator 10 is in an operational mode. As noted previously, the port number lamp 560 becomes illuminated (for example, in green) during the operational mode of the corresponding manipulator 10, and is extinguished during the stopped mode. Further, the lamp flashes during an automated origin point restoring operation, or during a resetting operation (stated otherwise, during automated modes), whereas during generation of an alarm state, the lamp flashes in red. In other words, the illuminated condition of the port number lamp 560 is switched simultaneously with the aforementioned LED 29.

One of the working unit type distinguishing lamps 562, 564, 566 is illuminated depending on the type of working unit 16 that is attached to the operating unit 14 of the manipulator 10, for showing the type of working unit. For example, the working unit type distinguishing lamp 562 is illuminated when the working unit 16 is a cutter, the working unit type distinguishing lamp 564 is illuminated when the working unit 16 is a gripper, and the working unit type distinguishing lamp 566 is illuminated when the working unit 16 is an electrical knife.

The connection confirmation lamp 568 is illuminated when it is determined that the connector 520 has been connected properly to a corresponding receptacle connector 572. The reset switch 570 is a lamp-incorporating switch, that becomes illuminated after the activate reset switch 554 has been pressed, at a time when a reset operation needs to be carried out on a corresponding manipulator 10. By pressing the reset switch 570 during a time when the reset switch 570 is illuminated, the motors 40, 41, 42 of the corresponding manipulator 10 carry out an automated origin point restoring operation under an action of the controller 514. While the reset operation is being carried out, the LED 29 and the port number lamp 560 undergo flashing, in order to indicate that the automated operation is currently underway.

The numbers "2" and "3" are printed on the port number lamps 560 of the second port 515*b* and the third port 515*c*, but otherwise, the second port 515*b* and the third port 515*c* have the same configuration as that of the first port 515*a*. The same reference numerals as those for the structural elements of the first port 515*a* have been used to indicate the structural elements of the second port 515*b* and the third port 515*c*, and descriptions of these features are omitted for the sake of brevity.

The first port 515*a*, the second port 515*b*, and the third port 515*c*, are surrounded respectively by frames having different colors (e.g., green, yellow, and blue) to enable them to be easily distinguished from each other. In particular, when corresponding colors also are applied to the connectors 520, recognition of the proper connector is made easier when the connectors 520 are reconnected.

The switches and lamps on the controller 514 are each provided with symbol markings, characters or abbreviations, which indicate the functions thereof. The switches and lamps are of a membrane type, whereby operability and durability thereof is superior.

In the foregoing manner, in the manipulator system 500 according to the present embodiment, by switching the illumination state of the port number lamps 560 and the operating unit LED 29 so as to indicate the operational mode and the stopped mode, the operator can easily recognize and distinguish at least between the operational mode and the stopped mode, so that surgical techniques can be implemented efficiently.

For example, upon detaching the working unit 16 from the operating unit 14, a time is required for each of the motors 40, 41, 42 to be restored to their predetermined origin points. Since this timing corresponds to the stopped mode, the operator confirms that the LED 29 has become extinguished, whereupon the working unit 16 can be safely detached. Conversely, when the LED 29 either is illuminated or flashing, it can be confirmed that it is not appropriate to detach the working unit 16 and predetermined responsive actions can be carried out. In this manner, the occurrence of attachment/detachment errors can be prevented.

Switching of the illumination states of the LED 29 and the port number lamps 560 is not limited to switching between ON and OFF states. Changing the illumination color, flashing cycle, or illumination brightness, etc., may also be used, whereby switching of the illumination state may be performed to enable confirmation by the operator.

The LED 29, which serves as an indicator, is disposed on the operating unit 14, where visual recognition thereof by the operator is facilitated so that generation of errors can be prevented more reliably. Among others, since the LED 29 is disposed on the upper surface of the bridge 28 at one location where visual recognition thereof by the operator is highest, confirmation of the mode at times when the working unit 16 is to be detached is made easier.

On the other hand, since the port number lamp 560, which also serves as an indicator, is disposed on the controller 514, it can be easily referred to and confirmed when the connector 520 is attached and detached, and further, confirmation of the mode can be confirmed thereby. Moreover, unlike the operating unit 14, there are not significant restrictions of available space on the controller 514, and the device can be made larger in scale, thereby enabling a greater amount of information to be displayed. As shown in FIG. 8, the port number lamps 560 have a larger surface area than the LED 29, which enables the port number to be displayed.

In addition, the controller 514 distinguishes and carries out control of a reset operation, as an automated mode wherein the motors 40, 41, 42 are operated regardless of whether an operating command is present or not, and causes the port number lamps 560 and the LED 29 to flash upon occurrence of the reset operation. In this manner, because flashing of the port number lamp 560 and the LED 29 is highly conspicuous, the fact that the motors 40, 41, 42 are undergoing automated operations can be easily confirmed in particular.

As an example of a situation in which the reset operation is needed, a situation may occur in which some trouble or malfunction occurs to the working unit 16 while work is being performed by the operator, whereupon it becomes necessary to detach the working unit 16 from the operating unit 14. Then, when another working unit 16 is attached, a case is indicated in which it is desirable for the motor shafts of the operating unit 14 to be returned to their origin points.

Furthermore, in the manipulator system 500 according to the present embodiment, when both the activate reset switch 554 and the reset switch 570 are operated in a predetermined sequence (that is, when the reset indicator lamp 556 is illuminated, the activate reset switch 554 is pressed, the reset switch 570 becomes illuminated, and thereafter the reset switch 570 is pressed), a reset operation for returning the actuators to predetermined origin points is carried out, so that the reset operation cannot be carried out inadvertently. The operation sequence for the activate reset switch 554 and the reset switch 570 is not limited to the aforementioned two-step sequence. A different sequence for operating both the activate reset switch 554 and the reset switch 570 may be used. For example, an operation in which both of the switches are pressed simultaneously may be included.

In the controller 514, it is preferable to provide three individual reset switches 570, whereby individual reset operations can be carried out with respect to each of the manipulators 10*a* to 10*c*. Further, there is only one activate reset switch 554, so that an unnecessary increase in the number of switches is avoided, thereby simplifying the configuration and improving operability.

The activate reset switch 554 and the reset switches 570 are disposed on the controller 514, so that unnecessary complexity in the structure of the manipulator 10 can be avoided, and the manipulator 10 can be made simple and light in weight, thus enhancing the operability thereof.

The controller 514 includes functions to detect errors individually with respect to three manipulators. For example, in the case that an error is generated at the first port 515*a*, the first ("1") port number lamp begins flashing, and when the activate reset switch 554 is pressed, the light emitting means of the reset switch 570 of the error-generating first port 515*a* is caused to emit light. Accordingly, operations are facilitated and erroneous operations can be prevented.

In the case that an error is generated in the manipulator 10*a* (see FIG. 1), an alarm display or the like is not carried out concerning the second port 515*b* and the third port 515*c*, regardless of the presence or absence of a connection of the connector 520 thereto. Consequently, the operator can easily confirm the fact that the manipulator 10*a* pertaining to the first port 515*a* is the manipulator for which a non-origin point detachment has occurred.

Next, the internal structure of the controller 514 shall be explained with reference to FIG. 8. To simplify matters, in FIG. 8, parts pertaining only to the first port 515*a* are shown, and parts of the second port 515b and the third port 515c have been omitted. In the configurations of the second port 515b and the third port 515c, certain parts thereof (for example, the computing section 110) are common with the first port 515a, whereas other parts (for example, the driver 116) are configured independently. Also, in FIG. 8, the structure of the front surface of the controller 514 (see FIG. 7) has been omitted and is not shown.

Figure 8:
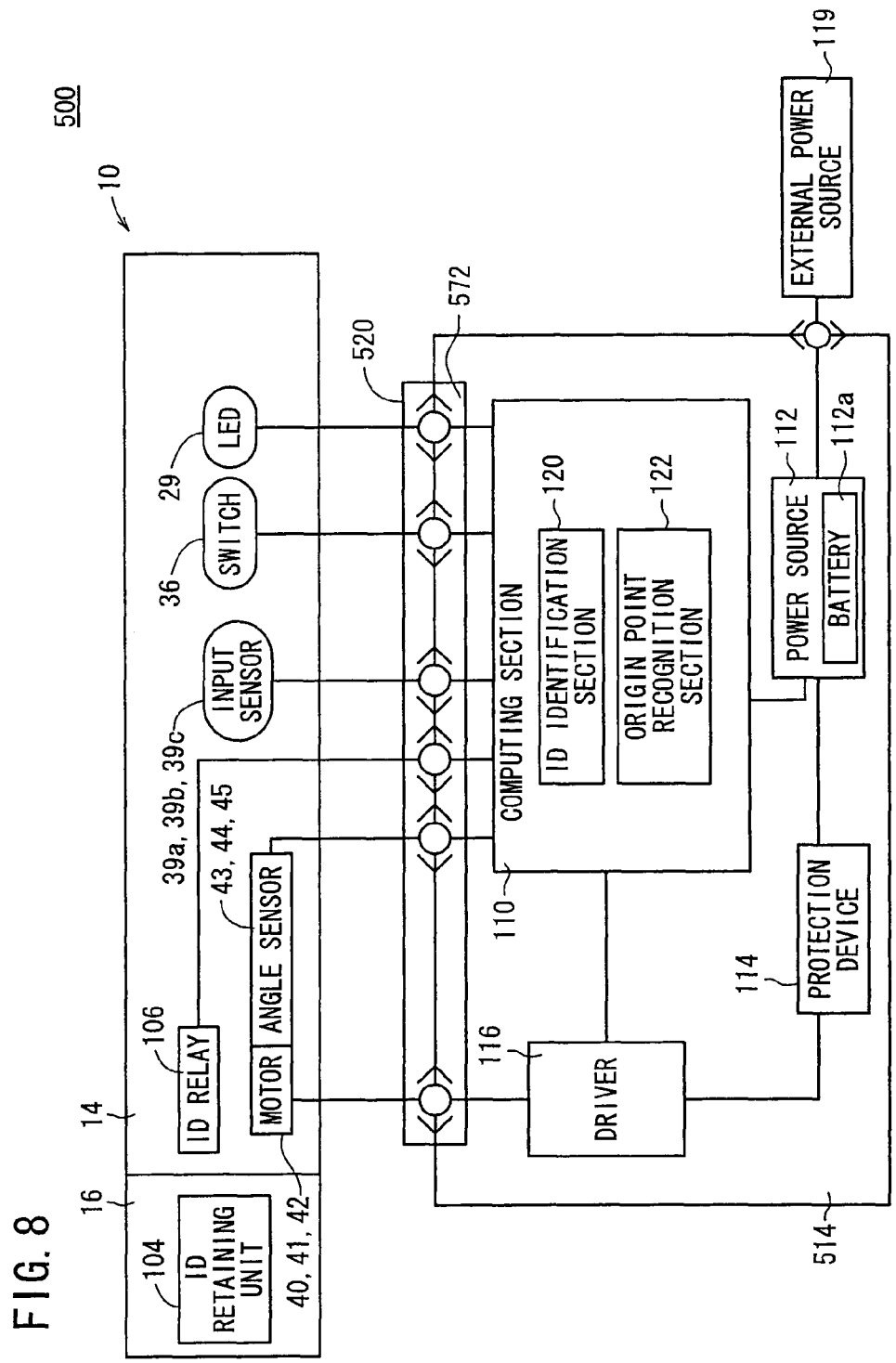
FIG. 8 is a schematic block diagram showing a configuration of the controller.

As shown in FIG. 8, the controller 514 includes a computing section (arithmetic processing section) 110, a power supply 112, a protection device 114, and a driver 116. The power supply 112 rectifies electrical power obtained from an external power source 119 to supply the electrical power to each part accordingly, together with performing charging of a battery 112a. A function is included therein such that, even in the case that electrical power is not supplied from the external power source 119, switching is performed automatically to supply power from the battery 112a, so that the power supply 112 operates as a so-called uninterrupted power source. The battery 112a may be connected, normally in parallel, with respect to an internal transformer/rectifier.

The protection device 114 serves to interrupt supply of power to the manipulator 10 based on various information such as computational period information from the computing section 110, driver information, predetermined stop commands and the like. By interrupting the electrical power of the driver 116 under operation of the protection device 114, movements and actions of the manipulator 10 can be halted instantaneously.

The computing section 110 is connected to angle sensors 43, 44, 45, input sensors 39a, 39b, 39c, and to the switch 36, and based on signals obtained from each of these components, determines operations of the manipulator 10 and supplies predetermined command signals to the driver 116, while also indicating predetermined state amounts to the operating state display device 530. The computing section 110 also is connected to the LED 29 for controlling the illumination state of the LED 29. Further, the computing section 110 is connected to and controls the operating state display device 530, the power source information display unit 532, the alarm unit 534, the activate reset unit 536, and the switches and lamps of each of the first port 515a, the second port 515b and the third port 515c, which are provided on the surface of the controller (see FIG. 7). The computing section 110 is constituted from components such as a CPU, a ROM, a RAM, etc., wherein by reading and executing a program, predetermined software based processing is carried out thereby.

The driver 116 is connected to the motors 40, 41, 42 and drives the motors 40, 41, 42 based on commands obtained from the computing section 110. Incidentally, as for the driving system for the motors 40, 41, 42, first, operation angle command values with respect to the distal end working unit are determined based on the input sensors 39a, 39b, 39c, deviations between such operation angle command values and the angle signals obtained from the angle sensors 43, 44, 45 are determined, and then based on such deviations, a predetermined compensation process is performed and command signals are supplied to the driver 116. Accordingly, the drive system for each of the motors 40, 41, 42 is formed as a closed-loop system.

The computing section 110 includes an ID identification section 120 and an origin point recognition section 122. The ID identification section 120 identifies the ID of the ID retaining section 104.

The computing section 110 determines conditions based on signals from the ID identification section 120, the origin point recognition section 122, the operating unit 14 and the like, and supplies electrical power, or stops the supply of electrical power, to the driver 116 under predetermined conditions, whereupon the motors 40, 41, 42 are controlled.

In the trigger lever 32 and compound input unit 34 (see FIG. 1), predetermined voltages are imposed on the input sensors 39a, 39b, 39c (potentiometers or the like), which serve to detect the amounts by which the trigger lever 32 and the compound input unit 34 are manually operated. The predetermined ranges of such voltages are set as operating ranges, and the controller 514 recognizes that an operating unit 14 has been detached based on the voltages supplied from the detectors being outside of the predetermined ranges. Accordingly, both the trigger lever 32 and the compound input unit 34 can be used dually as an operating amount input means, as well as a detachment recognition means for the operating unit 14. The origin point recognition section 122 recognizes whether the distal end working unit 12 is in a regulated (standard) origin point position or is in a non-origin point position, based on signals from the angle sensors 43, 44 and 45.

In the foregoing example, a manipulator system 500 having three connection ports was described, however, four or more connection ports may also be provided. In laparoscopic surgeries, there are cases in which three, or even four or more manipulators are used, or even in cases where only two manipulators are used at a time, it may be appropriate to provide a greater number as spare units, or in preparation for a next surgical technique.

Further, as a result of controlling two or more manipulators by means of a single controller 514, the computing section 110, etc., is used in common to control the manipulators, and therefore the effect of suppressing electrical power consumption is great.

Next, a lock mechanism 600, which can be applied and utilized in the controller 514, shall be described with reference to FIG. 9 and FIG. 10. The lock mechanism 600 serves to prevent a connector 520 from being pulled out at an inappropriate timing. Respective lock mechanisms 600 are provided for each of the first through third ports 515a to 515c.

Figure 9:
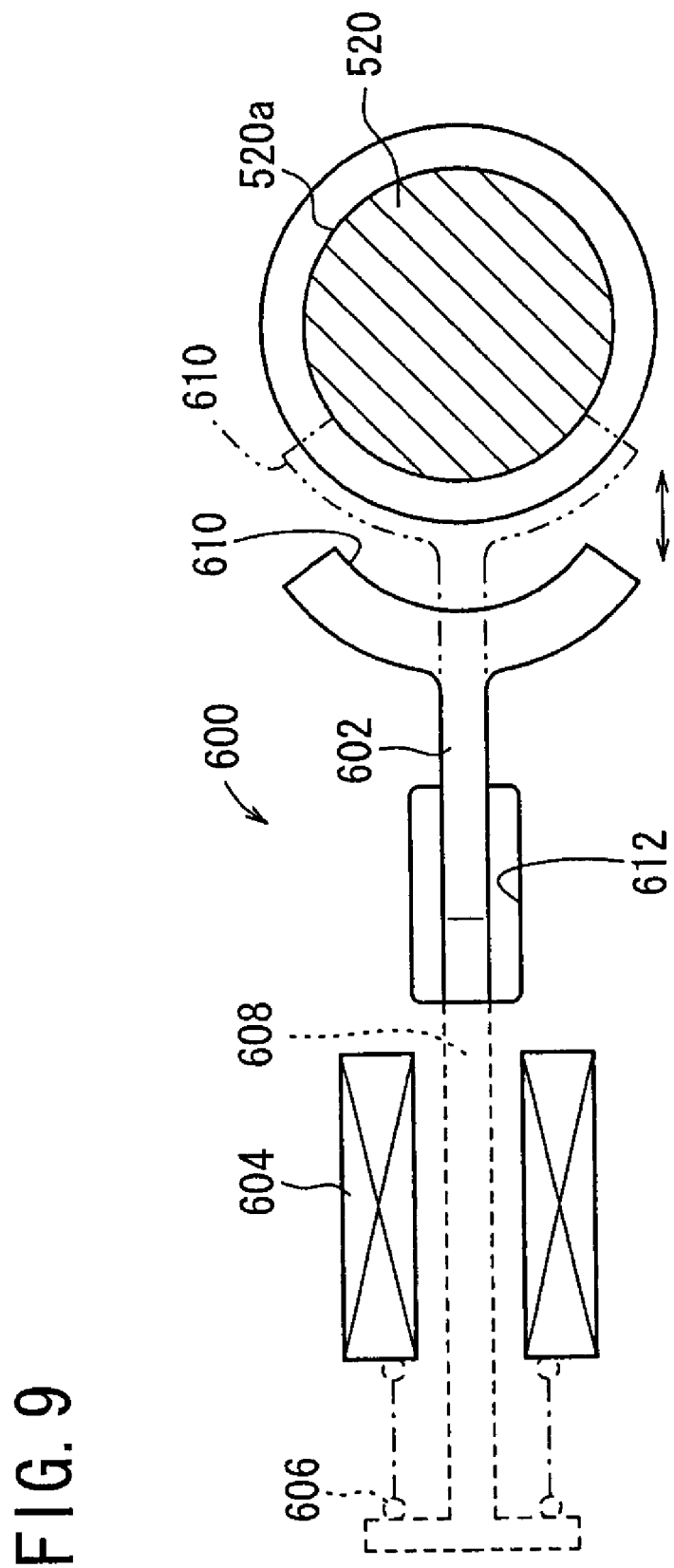
FIG. 9 is an outline frontal surface view of a lock mechanism.
Figure 10:
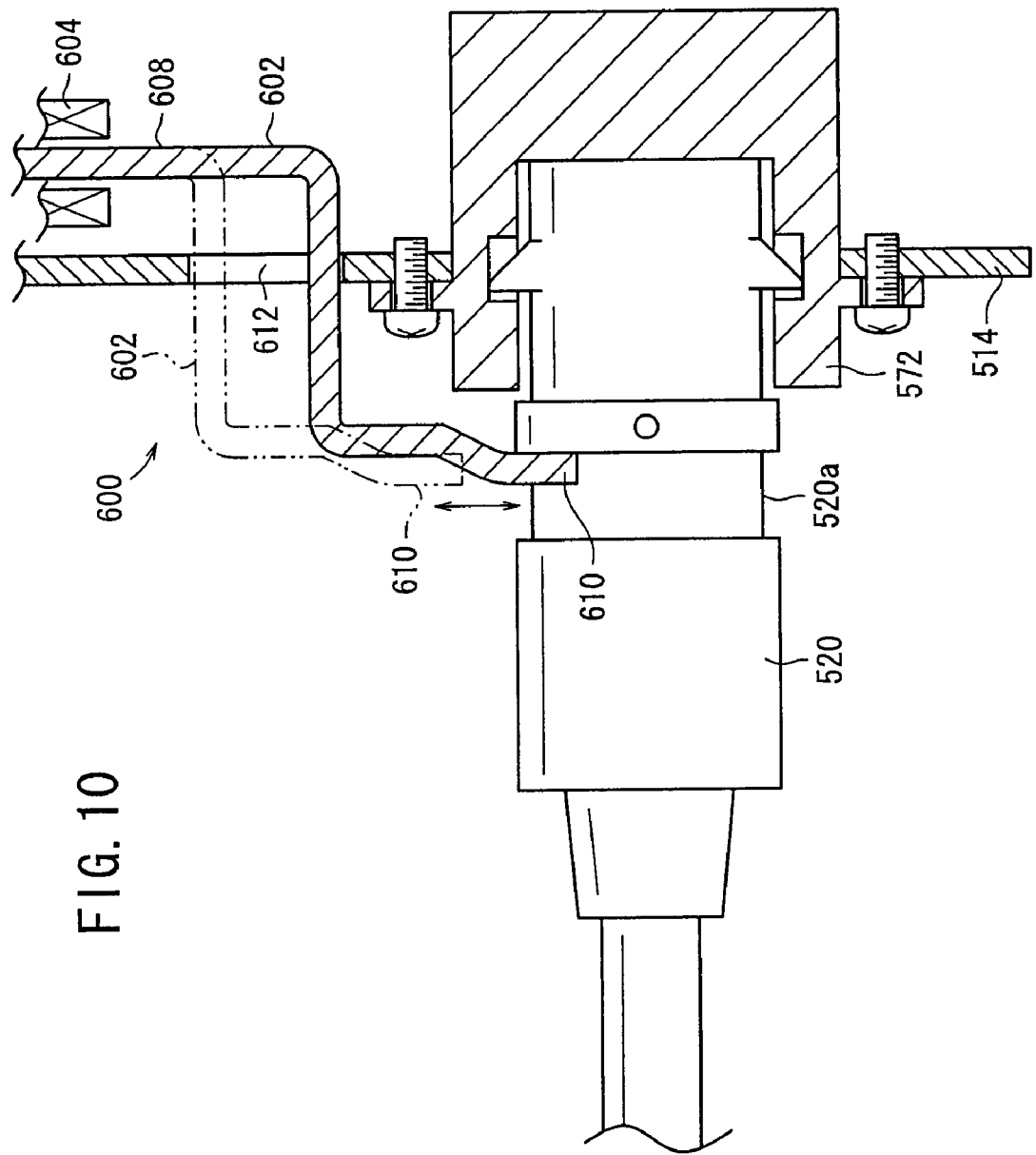
FIG. 10 is an outline cross sectional plan view of the lock mechanism.

As shown in FIGS. 9 and 10, the lock mechanism 600 includes a cam 602 disposed in the vicinity of the receptacle connector 572, a solenoid 604, which drives the cam 602 forward and backward in left and right directions as shown in FIG. 9, and a spring 606 that biases the cam 602 resiliently in a fixed direction. The cam 602 comprises a rod 608 inserted into the solenoid 604, and an engagement member 610 having an arcuate recessed shape on an end side thereof. The engagement member 610 is formed in a shape that engages in an annular recess 520a of the connector 520. The rod 608 and the solenoid 604 are arranged inside the controller 514. The rod 608 is bent and projects outwardly from an elongate hole 612 disposed on the front surface of the controller 514 so that the engagement member 610 is exposed on the front surface. Because the location where the connector 520 and the engagement member 610 engage with each other is on the front surface side of the controller 514, locked and unlocked states of the connector 520 can be confirmed visually.

A magnetic force in the solenoid 604 is generated and cutoff under an action of the computing section 110. At times when the solenoid 604 is not magnetically excited, the cam 602 is positioned to the lefthand side, as shown in FIG. 9, by the resilient force of the spring 606, thereby enabling detachment of the connector 520 with respect to the receptacle connector 572.

At times when the solenoid 604 is magnetically excited, the cam 602 is moved to the righthand side, as shown in FIG. 9, while opposing the resilient force of the spring 606, whereupon the end of the engagement member 610 engages in the annular recess 520*a* of the connector 520. Consequently, in this condition, the connector 520 is prevented from being pulled out from the receptacle connector 572.

The lock mechanism 600 is not limited to this type of structure, and other configurations may be provided in which pulling out of the connector 520 is prevented under an operation of the controller 514. The actuator for driving the cam 602 is not limited to the solenoid 604, and motor and gear mechanisms or the like may also be used. Movement of the cam 602 is not limited to a linear motion type. For example, the cam 602 may be of a tilting type. The location where the engagement member 610 engages with the connector 520 is not limited to being on the front surface side of the controller 514, and engagement inside of the controller 514 also is feasible.

As for the timing at which the solenoid 604 is excited, the solenoid 604 is excited in the case of the operational mode (or stated otherwise, at a timing when the switch 36 is placed in an ON state and the port number lamp 560 and the LED 29 are illuminated in green). The timing at which the solenoid 604 is non-excited occurs when the operational positions of all the motors 40, 41, 42 are at their origin points, and moreover, in the case of the stopped state (or stated otherwise, at a timing when the switch 36 is placed in an OFF state and the port number lamp 560 and the LED 29 are extinguished).

In this manner, in those cases where it is possible for the operational state of the motors 40, 41, 42 to be at axial positions apart from their origin points, due to locking of the connector 520 by the lock mechanism 600, the connector 520 cannot be pulled out and become detached inadvertently. Therefore, the system is favorable in that, when a connector 520 is attached at a subsequent time, each of the motors 40, 41, 42 can be matched reliably with their respective origin positions.

Further, after performing a predetermined reset operation, the solenoid 604 is placed in a non-excited state, whereupon the connector 520 can be pulled out. Consequently, inadvertent pulling out of the connector 520 at times when the operational mode is in effect can be prevented.

The manipulator system 500 and controller 514 have been described as pertaining to applications for medical uses in which the manipulator is handled and operated directly by an operator. However, the intended use thereof is not necessarily limited to such uses. For example, the invention may be applied to a remote operation mechanism for performing medical techniques through an electronic communications means or the like, at a location separated from the patient.

The medical manipulator system according to the present invention is not limited to the aforementioned embodiments. It should be understood that various other configurations may be adopted without deviating from the scope of the invention as set forth in the appended claims.

What is claimed is:

1. A medical manipulator system having a medical manipulator, a controller, and at least one indicator for indicating an operational state of the medical manipulator, the medical manipulator system comprising:
    an operating unit equipped with the at least one indicator, an actuator, a grip handle that is gripped manually, and an input unit for inputting operation commands; and
    a working unit being detachable with respect to the actuator and being equipped with a distal end working unit, the distal end working unit being operatively coupled to the actuator at an end of a shaft, and being rotated about a pivot axis that is non-parallel with an axis of the shaft,
    wherein the controller controls the actuator based on an operation command supplied from the input unit, and a first control is carried out for distinguishing at least between an operational mode in which the operation command is validated and the actuator is driven, and a stopped mode in which the actuator is halted regardless of whether the operation command is present or not, an illuminated state of the at least one indicator being switched by the operational mode and the stopped mode, and
    wherein in the controller, a second control is carried out for distinguishing an automated mode in which the actuator is driven regardless of whether the operation command is present or not, the at least one indicator flashing by the automated mode.

2. The medical manipulator system according to claim 1, wherein the operating unit comprises:
    an actuator unit in which the actuator is disposed; and
    a bridge interconnecting the grip handle and the actuator unit,
    wherein the at least one indicator is disposed on an upper surface or a side surface of the bridge.

3. The medical manipulator system according to claim 1, wherein another indicator is provided on the controller, and an illuminated state of the other indicator is switched simultaneously with that of the one indicator.

4. The medical manipulator system according to claim 1, the operating unit further comprising a switch for switching an operational state of the medical manipulator, and
    the controller reads in a state of the switch, and places the medical manipulator in the operational mode when the switch is in a first state, places the medical manipulator in the automated mode when the switch is switched from the first state to a second state, and returns the actuator to a predetermined origin point and then places the medical manipulator in the stopped mode after the actuator has been returned to the origin point.

* * * * *